(12) United States Patent
Dennerlein et al.

(10) Patent No.: US 8,588,497 B2
(45) Date of Patent: Nov. 19, 2013

(54) METHOD FOR CORRECTION OF ARTIFACTS ARISING FROM TEMPORAL CHANGES OF ATTENUATION VALUES

(75) Inventors: Frank Dennerlein, Forchheim (DE); Andreas Fieselmann, Erlangen (DE)

(73) Assignee: Siemens Aktiengesellschaft, München (DE)

( * ) Notice: Subject to any disclaimer, the term of this patent is extended or adjusted under 35 U.S.C. 154(b) by 91 days.

(21) Appl. No.: 13/221,964

(22) Filed: Aug. 31, 2011

(65) Prior Publication Data

US 2012/0051619 A1 Mar. 1, 2012

(30) Foreign Application Priority Data

Aug. 31, 2010 (DE) .......................... 10 2010 040 041

(51) Int. Cl.
*G06K 9/00* (2006.01)

(52) U.S. Cl.
USPC ......................................................... 382/131

(58) Field of Classification Search
None
See application file for complete search history.

(56) References Cited

U.S. PATENT DOCUMENTS

| 8,280,135 | B2 * | 10/2012 | McCollough et al. ........ 382/128 |
| 2004/0136608 | A1 | 7/2004 | Rosenfeld |
| 2005/0135664 | A1 | 6/2005 | Kaufhold et al. |
| 2006/0062442 | A1 * | 3/2006 | Arnaud et al. ................ 382/128 |
| 2006/0074290 | A1 * | 4/2006 | Chen et al. ..................... 600/407 |
| 2006/0078182 | A1 | 4/2006 | Zwirn et al. |
| 2008/0107229 | A1 * | 5/2008 | Thomas et al. ................... 378/4 |
| 2008/0219534 | A1 * | 9/2008 | Faul et al. .................... 382/131 |
| 2009/0110256 | A1 * | 4/2009 | Thielemans et al. .......... 382/131 |
| 2009/0324047 | A1 * | 12/2009 | Jarisch ........................... 382/131 |
| 2010/0128954 | A1 * | 5/2010 | Ostrovsky-Berman et al. ............................. 382/131 |
| 2010/0183214 | A1 * | 7/2010 | McCollough et al. ........ 382/131 |
| 2010/0215238 | A1 * | 8/2010 | Lu et al. ........................ 382/131 |
| 2011/0103669 | A1 * | 5/2011 | Michel et al. ................. 382/131 |
| 2012/0051619 | A1 * | 3/2012 | Dennerlein et al. .......... 382/132 |

FOREIGN PATENT DOCUMENTS

| CA | 2360656 A1 | 4/2002 |
| DE | 102006049664 A1 | 5/2008 |

OTHER PUBLICATIONS

Nuyts. et al., "Simultaneous maximum a-posteriori reconstruction of attenuation and activity distributions form emission sinograms", IEEE Trans Med Imaging, 1999; 18(5): 393-403.*
Montes et al., "A temporal interpolation approach for dynamic reconstruction in perfusion CT" Medical Physics, 2007, pp. 3077-3092, vol. 34, No. 7.
Fieselmann et al., "A dynamic reconstruction approach for cerebral blood flow quantification with an interventional C-arm CT", Proc. IEEE ISBI, 2010, pp. 53-56.

(Continued)

*Primary Examiner* — Bhavesh Mehta
*Assistant Examiner* — Tahmina Ansari

(57) ABSTRACT

A method for correcting artifacts in an image dataset reconstructed by filtered back projection is proposed. The artifacts are occurred as a result of temporal changes of attenuation values during rotational recording of X-ray projection images with an angular speed. A linear, analytically-derived, filter-type relationship between the attenuation values of the image dataset at a reference point and the real attenuation values is determined from the sum of a respective application of an angle speed-dependent weighting factor, a point spread function and a temporal derivation, evaluated at the reference time. The linear relationship is inverted and the inverted linear relationship is applied to the attenuation values of the image dataset for the correction.

11 Claims, 2 Drawing Sheets

(56) References Cited

OTHER PUBLICATIONS

Serowy et al. "A Jacobi-like Solution to the Model Based Tomographic X-Ray Perfusion Imaging", Proc. IEEE Nuclear Science Symposium onference Record, 2007, 4, pp. 3085-3088.

Christoph Neukirchen et al., "An Iterative Approach for Model-Based Tomographic Perfusion Estimation" Proc. $9^{th}$ International Meeting on Fully Three-Dimensional Image Reconstruction in Radiology and Nuclear Medicine, 2007, pp. 104-107.

* cited by examiner

METHOD FOR CORRECTION OF ARTIFACTS ARISING FROM TEMPORAL CHANGES OF ATTENUATION VALUES

CROSS REFERENCE TO RELATED APPLICATIONS

This application claims priority of German application No. 10 2010 040 041.6 filed Aug. 31, 2010, which is incorporated by reference herein in its entirety.

FIELD OF THE INVENTION

The invention relates to a method for correction of artifacts arising from temporal changes of attenuation values during rotational recording of one or more two-dimensional projection images with an angular speed in a two-dimensional or three-dimensional image dataset of a target region, especially one reconstructed by means of a filtered back projection.

BACKGROUND OF THE INVENTION

The reconstruction of two-dimensional image datasets from one-dimensional image datasets or of three-dimensional image datasets from two-dimensional image datasets has long been known in X-ray imaging, for which different reconstruction methods are known, for example filtered back projection and iterative reconstruction. The projection images are recorded in such cases in a chronological sequence from different projection angles, whereby X-ray emitter and detector mostly describe an orbital trajectory.

A problem always arises if, during a recording process, i.e. from the recording of the first projection image through to the recording of the last projection image, the attenuation values at specific points of the target region change over time. This will be explained in more detail with reference to an example.

Strokes are the third most frequent cause of death in Western countries. Intra-arterial thrombolysis can be used for their treatment in which a medicament is administered through a catheter into a brain artery, with the aid of which the thrombus can be removed or which dissolves the latter. In such cases it is helpful, shortly before and/or during and/or after the intervention, to carry out a tomographic blood flow measurement through perfusion imaging.

In such cases current known methods are perfusion CT imaging and perfusion MR imaging, in which a contrast agent is injected and a series of image datasets are recorded in order to observe the spreading out of the contrast agent in the patient's vascular system. Time-attenuation curves can then be identified from the image datasets, from which the blood flow, in the example the cerebral blood flow, is determined.

Since these types of interventions are frequently undertaken with the support of a C-arm X-ray device, for example an angiography system, it would be of great advantage for the workflow in the interventions if the perfusion imaging were able to be carried out with a C-arm.

For standard reconstruction methods however it is a prerequisite that the attenuation values remain at least essentially constant over time during the recording of the projection images. Since the rotation time of the C-arm with the X-ray emitter and the detector, which can typically amount to between three and five seconds, is however significantly longer than that of a CT device, which can typically amount to 0.5 seconds, artifacts are produced in the slower C-arm recordings, which are the result of changes in the attenuation values caused by the inflow or outflow respectively of contrast agent. These falsify the results however.

To solve these problems there are already two known solutions in the prior art.

It has thus been proposed that a dynamic approach to reconstruction be selected in order to reconstruct a perfusion dataset from projection images recorded with a C-arm X-ray device. This approach is based on a similar method to algebraic reconstruction techniques and is described in articles by Serowy, S. et al., "A Jacobi-like Solution to the Model Based Tomographic X-Ray Perfusion Imaging", Proc. IEEE NSS/MIC, 2007, 4, pages 3085 to 3088, and also C. Neukirchen and S. Hohmann, "An Iterative Approach for Model-Based Tomographic Perfusion Estimation". Proc. Fully-3D, 2007, pages 104 to 107. However this method is extremely slow and thereby inefficient. In addition the proposed optimization methods can create solutions which only correspond to local minima and thus deliver an unsatisfactory image quality.

It has further been proposed that a dynamic reconstruction algorithm be selected which builds on the filtered back projection to reduce the inconsistency by a temporal interpolation method. This method is described in articles by P. Montes and G. Lauritsch, "A Temporal Interpolation Approach for Dynamic Reconstruction in Perfusion CT", Med. Phys. 2007, 34, pages 3077 to 3092, and also A. Fieselmann et al., "A Dynamic Reconstruction Approach for Cerebral Blood Flow Quantification with an Interventional C-arm CT", Proc. IEEE ISBI, 2010, pages 53 to 56. This method too is rather slow and is not optimally suited to typical recording geometries of C-arm angiography systems, in which the C-arm rotates alternately in different directions.

SUMMARY OF THE INVENTION

The underlying object of the invention is thus to specify a method with which an improved and especially fast correction of artifacts resulting from changes to the attenuation values over time during the recording of the projection images is possible, especially in perfusion imaging.

To achieve this object the invention makes provision in a method of the type described at the outset for a linear, analytically-derived filter-type relationship between the attenuation values of the image dataset and a reference time and the real attenuation values to be used, in which the attenuation values of the image dataset are produced from a sum of an application of each case of an angular speed-dependent weighting factor, a point spread function and a temporal derivation evaluated at the reference time, whereby the linear relationship is inverted and for correction the inverted linear relationship is applied to the attenuation values of the image dataset.

In this case it should be noted in advance that a zero derivation at the reference time results in the evaluation of the function at the reference time, as is known.

The invention is thus based on the underlying knowledge that the relationship between the attenuation values of the image dataset and the real attenuation values can be analytically derived and transferred into an invertible relationship. This is possible for different recording geometries, for example fan beam geometry, parallel beam geometry or cone beam geometry, in that for example the time dependency over the projection angle of the individual projection images actually recorded after each other in time is encrypted, the time dependency of which is actually known in its turn, can be deduced from the angular speed for example. Thus if the known formula for the projections is written at the different angles time-dependent and if this formula is combined with the likewise known, time-dependent formulated formula for the filtered back projection, this produces a formula which can be expressed as a filter model in which the reconstructed attenuation values of the image dataset are produced as a spatial integral over a contribution function evaluated over a reference period, in which the real attenuation values are also contained.

If in the contribution function a Taylor development is used around the reference time, which can for example be formulated as the central point in time of the recording period of the projection images, for the real attenuation values, a linear relationship with analytically-definable operators is ultimately produced, since the temporal derivations are a linear operation, here the temporal derivation evaluated at the reference time, a weighting factor and a point spread function, whereby as a result of the Taylor development a point spread function and a weighting factor are always assigned to a temporal derivation.

The linear relationship can thus be described by the formula $$a = \left(\sum_i W_i P_i D_i\right) b,$$

wherein a is a vector describing the measured attenuation values, b is a vector describing the real attenuation values, $W_i$ is a diagonal matrix specifying the weighting factor, $P_i$ is a matrix describing the point spread function and $D_i$ is a matrix describing an ith-order temporal derivation. The term zero order in this case, if the associated weighting factor is one, can simply be produced as the point spread function $P_0$ which then actually also corresponds to the static case: The smearing is defined by the (static) point spread function. Thus in this notation and actual linear filter model is produced.

Overall the individual contributions can thus be described in their sum as a single matrix A, so that a=Ab then applies. The Matrix A can be automatically analytically determined and correspondingly also, for example via a known inversion algorithm, be inverted, $b=A^{-1}a$, so that the real attenuation values at the reference time can be obtained. In such cases there can be provision for the inverted linear relationship to be determined by a singular value decomposition, whereby other algorithms are naturally also able to be used.

How many terms actually have to be taken into consideration, especially with regard to the temporal derivations, is given by the type of time dependency, with usually the first and if necessary the second derivation being able to be sufficient; this will be explained in greater detail below for the perfusion example.

Thus a summary of the inventive proposals is that the filtered back projection of a temporally-dynamic object be described as a filter, which is able to be mathematically exactly derived. This means that if the input signal (for example the change over time of the contrast agent concentration in an artery) is precisely known the reconstructed image datasets can be defined with the aid of the filter described by the relationship. The filter can be mathematically exactly derived, which has been shown within the context of the development of the present invention.

As has just been shown, the filter can be described as a linear equation system (Matrix A). Thus the filter can be inverted in order to eliminate and/or to reduce reconstruction artifacts.

In this case filtered back projection, which is known to operate very quickly, can thus be used especially advantageously as the reconstruction method. This means that the method is already faster than the algebraic approaches. A further advantage of the present invention is that the method can be easily adapted to different directions of rotation, for example of a C-arm.

In an especially advantageous embodiment of the present invention there can be provision however for the correction to be applied locally, especially in the region of an artifact and/or of a structure at risk from artifacts, especially a blood vessel. This is possible since the convolutional kernel is locally restricted: Both the point spread function and also the derivation are local operations so that the inventive method can be used in a small subregion of the image dataset, which reduces the size of the matrixes to be inverted and thus further greatly accelerates the method and constitutes an advantage in relation to the prior art described at the outset. Corrections can for example, by artifacts being identified in the image dataset or by prior knowledge about regions at risk from artifacts being used, the position of large blood vessels, especially of arteries, in the case of perfusion imaging for example, specifically only be undertaken where they are needed so that the overall processing time is greatly reduced. Such local regions can, in a two-dimensional image dataset reconstructed from one dimensional projection images, typically have a size of 40 times 40 pixels for 40 time steps, i.e. 40 projection images.

Naturally however it is also conceivable for the entire image dataset and/or a selected region of the image dataset to be broken down into units to be corrected locally. In such cases values can be selected which correspond in particular to the effective region of the point spread function and/or which can be computed quickly and stably with the algorithms used. In the three-dimensional case in which two-dimensional projection images are reconstructed to a three-dimensional image dataset, it has been shown that the correction can typically be undertaken in slices, since for example with cerebral blood flow measurements in the z-direction only a slight scattering is present.

There can further be provision for the location of the structure to be determined automatically, especially by means of an anatomical atlas. If, such as in perfusion imaging for example, it is known from the start that problems are to be expected for example in the speed of travel in arteries, the position of these arteries as a structure at risk from artifacts can be defined in advance from an anatomical atlas, so that corrections can then be undertaken automatically locally around the structures, without it being necessary for a user to intervene to select the regions.

As already mentioned, an especially advantageous are of application of the inventive method lies in perfusion imaging, so that there can be provision for the rotation imaging to be undertaken within the framework of perfusion imaging, especially with a C-arm. In this way artifacts can be reduced and a more precise determination of the blood flow is typically possible. The inventive method also allows use of perfusion imaging on X-ray devices with a C-arm, which in any event are frequently to be found in a room for interventions in which such information is needed. Perfusion time curves are frequently able to be temporally locally linearized or at least second-order approximated (typically if the recording includes reaching the maximum speed of travel and slow decay) so that expediently there can be provision for the terms of the sum only to be considered up to the first derivation or up to the second derivation. The computing effort is thus further reduced and the method can be carried out more quickly.

In a further advantageous development of the present invention there can be provision, for determining the point spread function assigned to an nth derivation, for a real attenuation point described in time by an nth-level polynomial to be projected forward and for the point spread function to be determined from this by back projection. It is thus possible also to determine the point spread function within the framework of a simulation measurement by observing one point with an attenuation value which changes over time. This can be used within the framework of a forward projection to obtain virtual projection images which, to obtain the point spread function, are then reconstructed as normal. In such cases attention should naturally be paid to the normalization. The advantage of such a method of operation is that the analytically-determined relationship is based on a perfect trajectory, which is not always available in reality. The deviations are known however so that account can also be taken of them within the framework of such a simulation, so the method becomes even more exact. In concrete terms, for determining the zero-order point spread function, a constant temporal attenuation value curve can typically be used, a linear curve for the first order etc.

It should be noted generally at this point that the inventive method can also be advantageously employed within the framework of perfusion tomosynthesis, where a reconstruction, preferably of a non-axial slice, is carried out from a restricted projection angle interval. It is also applicable for reconstructions in which the available projections are recorded with a greater angle difference, for example of 5° instead of 1°. Also in such cases the point spread functions of zero and higher order that are used in the filter model can be calculated.

BRIEF DESCRIPTION OF THE DRAWINGS

Further advantages and details of the present invention emerge from the exemplary embodiments described below as well with reference to the drawing, in which.

DETAILED DESCRIPTION OF THE INVENTION

Figure 1:
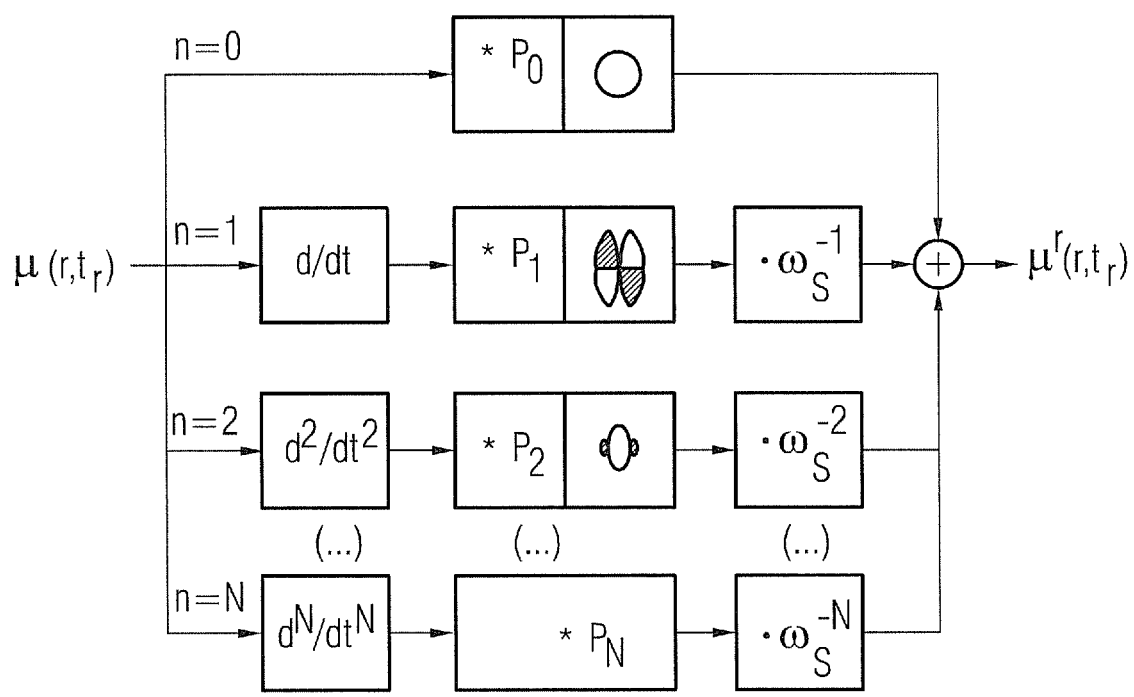
FIG. 1 shows a schematic diagram of the filter model.

The inventive method is explained below for the purposes of simplifying the presentation for the case of a reconstruction of a two-dimensional image dataset from one-dimensional projection images which are recorded using different projection geometries, i.e. projection angles, lying on a trajectory. Naturally what is described here can also be applied to the reconstruction of three-dimensional image datasets from two-dimensional projection images, whereby for example the Feldkamp algorithm of filtered back projection can be used.

The derivation of the filter model used will initially be outlined for the case of fan beam geometry.

It is assumed that the X-ray emitter rotates at a constant angular speed of $\omega_s$ on a trajectory of radius R around the origin of the coordinate system. The position $a(\lambda(t))$ of the source at time t can then be written as:

$$a(\lambda(t)) = (R \cos(\lambda(t)), R \sin(\lambda(t)))^T \quad (1)$$

$$\lambda(t) = \omega_s \cdot t + \lambda_0 \quad (2)$$

wherein $\lambda(t)$ is the angular position of the X-ray emitter at time t and $\lambda_0$ is the angle at time t=0. For time-dependent attenuation values $\mu(x, \lambda(t))$ at positions $x=(x, y)^T$ the projections $p(\lambda(t), \gamma)$ at the fan angle $\gamma$ can be written with the usual definition of the $\delta$ function:

$$p(\lambda(t), \gamma) = \int\int_{-\infty}^{+\infty} \mu(x, \lambda(t)) \cdot \delta(\gamma^*(x, \lambda(t)) - \gamma) dx dy, \quad (3)$$

wherein $\gamma^*(>=x, \lambda)$ defines the fan beam angle at the X-ray source position $\lambda$ which intersects with the pixel at point x. This angle can be computed to $$\gamma^*(x, \lambda(t)) = \arctan\left(\frac{x \cdot e_u(\lambda)}{R - x \cdot e_w(\lambda)}\right), \quad (4)$$

wherein the unity vectors $e_u=(-\sin(\lambda), \cos(\lambda))^T$ and $e_w=(\cos(\lambda), \sin(\lambda))^T$ are used. The attenuation value $\mu^r(r,t_r)$ at a location r at the reference time $t_r$ can be written by filtered back projection:

$$\mu^r(r, t_r) = R \int_{-\infty}^{+\infty} \frac{1}{\|r - a(\lambda(t))\|^2} \quad (5)$$
$$\int_{-\infty}^{+\infty} p(\lambda(t), \gamma) g(\gamma^*(r, \lambda(t)) - \gamma) \cos(\gamma) w(\lambda(t) - \lambda(t_r), \gamma) d\gamma dt$$

with $$g(\gamma) = \left(\frac{\gamma}{\sin(\gamma)}\right)^2 \cdot h_{ramp}(\gamma), \quad (6)$$

wherein $h_{ramp}(\gamma)$ is the ramp filter. The function $w(\lambda, \gamma)$ is a sliding window function which also compensates for redundant data in the fan beam geometry. The function $w(\lambda, \gamma)$ is zero outside an angle interval of length $\lambda_D$ and assumes function values $m(\lambda, \gamma)$ within this interval. The function $m(\lambda, \gamma)$ can be selected for example as in the article by F. Noo et al., "Image reconstruction from fan-beam projections on less than a short scan", Phys. Med. Biol. 47, 2002, 2525-2546.

If formulae (3) and (5) are now combined and if the sequence of integration changes and evaluates the convolution with the Delta function, the following equations are obtained $$\mu^r(r, t_r) = \int\int_{-\infty}^{+\infty} \chi(x, r, t_r) dx dy \quad (7)$$

$$\chi(x, r, t_r) = \quad (8)$$
$$R \int_{-\infty}^{+\infty} \frac{1}{\|r - a(\lambda(t))\|^2} \mu(x, \lambda(t)) \cdot g(\gamma^*(r, \lambda(t)) - \gamma^*(x, \lambda(t))) \cdot \ldots$$
$$\cos(\gamma^*(x, \lambda(t))) \cdot w(\lambda(t) - \lambda(t_r), \gamma^*(x, \lambda(t))) dt.$$

Equations (7) and (8) can be interpreted as a filter which transforms the real attenuation values $\mu$ into the reconstructed attenuation values $\mu^r$ of the image dataset. The function $\chi(x, r, t_r)$ can be understood as the contributions of the locations x to the reconstruction r.

Now the Taylor development of $\mu(x, \lambda(t))$ by $\lambda(t_r)$ is computed, in order to compute the properties of $\chi(x, r, t_r)$ in relation to the derivations of $\mu$.

$$\mu(x, \lambda(t)) = \sum_{n=0}^{\infty} \frac{d^n \mu(x, \lambda(t))}{d\lambda^n}\bigg|_{t=t_r} \cdot \frac{(\lambda(t) - \lambda(t_r))^n}{n!} \quad (9)$$

It is assumed here that $\mu(x, \lambda(t))$ in the interval can be expressed as a Taylor sequence that corresponds to the current sliding window w. This is possible since the changes over time, especially within the framework of the perfusion, are in practice continuous, low-frequency functions. Looking at equation (2), it can be seen that second and higher-order derivations of $\lambda(t)$ disappear and the following is obtained:

$$\frac{d^n \mu(x, \lambda(t))}{dt^n}\bigg|_{t=t_r} = \frac{\partial^n \mu(x, \lambda(t))}{\partial \lambda^n}\bigg|_{t=t_r} \cdot \left(\frac{d\lambda(t)}{dt}\bigg|_{t=t_r}\right)^n. \quad (10)$$

If (8), (9) and (10) are now combined and if the order of sum and integration are changed, the result finally obtained is $$\chi(x, r, t_r) = \sum_{n=0}^{\infty} \frac{d^n \mu(x, \lambda(t))}{dt^n}\bigg|_{t=t_r} \cdot \omega_s^{-n} \cdot P_n(x, r, \lambda(t_r)) \quad (11)$$

with $$P_n(x, r, \lambda(t_r)) = \quad (12)$$
$$\frac{R}{n!} \int_{-\infty}^{+\infty} \frac{(\lambda(t) - \lambda(t_r))^n}{\|r - a(\lambda(t))\|^2} \cdot g(\gamma^*(r, \lambda(t)) - \gamma^*(x, \lambda(t))) \cdots$$
$$\cos(\gamma^*(x, \lambda(t))) \cdot w(\lambda(t) - \lambda(t_r), \gamma^*(x, \lambda(t)))dt.$$

In such cases $P_n(x, r, \lambda(t_r))$ can be interpreted as the point spread function which is weighted with the nth temporal derivation of $\mu(r,t_r)$ and the inverse angular speed $\omega_s$ of the X-ray emitter. Here in this exemplary embodiment the center of the sliding window is expediently selected as angle $\lambda(t_r)$.

FIG. 1 shows a diagram of the filter model processed in this way, whereby a possible appearance of the point spread function $P_n$, has also been indicated.

A similar derivation is also possible for other geometries, whereby the filter model basically, if a vector containing the attenuation values of the image dataset or the real attenuation values is used as a and b in each case, can be written as a linear equation system:

$$a = \left(\sum_i W_i P_i D_i\right) b = Ab, \quad (13)$$

wherein $W_i$ is a diagonal matrix containing the weighting, $P_i$ is the matrix describing the respective point spread function and $D_i$ is a matrix describing an nth-degree differentiation according to time (for example forming a difference between adjacent points in time).

For correction of artifacts the relationship (13) is now used in that the matrix A is inverted by a singular value decomposition for example.

Figure 2:
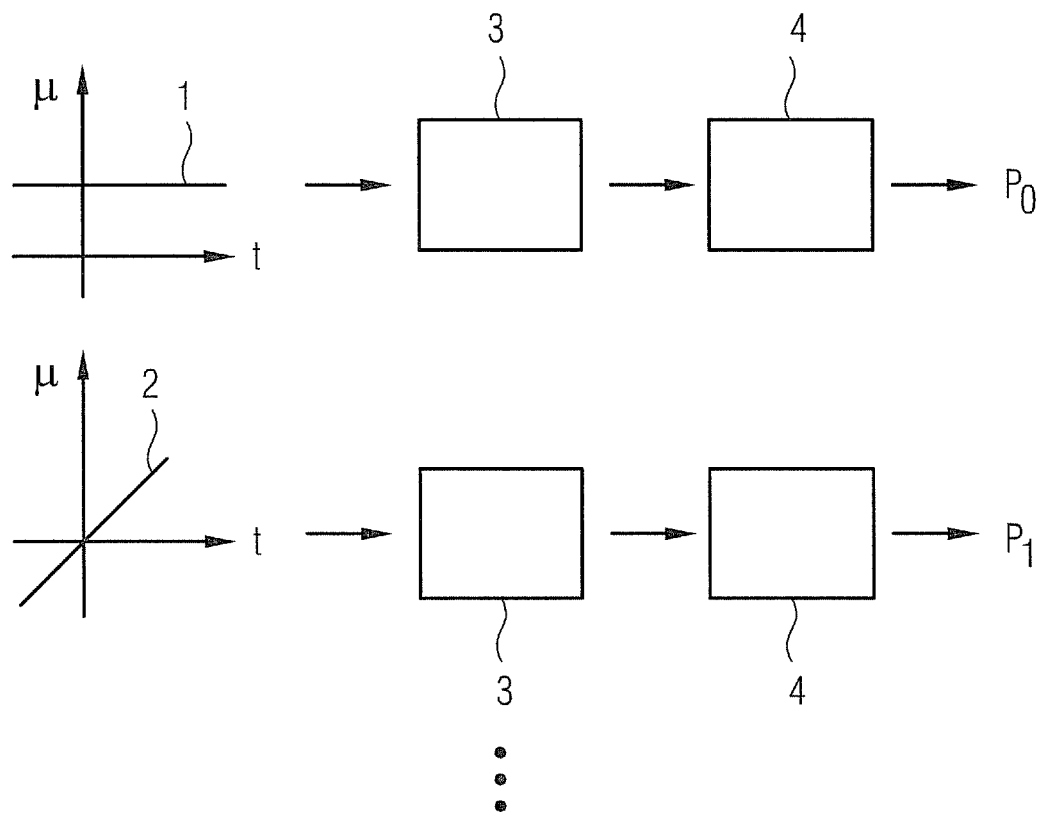
FIG. 2 shows a diagram for determining the point spread function from a simulation and
FIG. 3 shows a possible artifact and its reduction.

The point spread functions in this case can be analytically computed, however a type of "calibration" can also take place in the simulation in order to be able to take account of deviations from an ideal trajectory. This is shown schematically in FIG. 2 for $P_0$ and $P_1$.

The starting point is a point in space, especially in the origin of the coordinate system, the attenuation value of which follows a specific temporal curve. For the zero order a constant temporal curve 1 is assumed, for example at one, for the first order a linear gradient 2 for example with a slope of one.

For these points with their curves there is now forward projection in a step 3, meaning that virtual projection images are determined, which then in a step 4 are reconstructed by means of filtered back projection to an image dataset which corresponds to the point spread functions. In this case deviations from an ideal trajectory geometry can be taken into account in steps 3.

Naturally point spread functions of higher order can also be determined in this way, whereby however attention must be paid to normalization in all cases.

An actual sequence of the inventive method can then typically be arranged as follows. Initially the matrixes describing the point spread functions will be determined, be it computationally or using a simulation in accordance with FIG. 2, and typically maintained for a number of correction processes.

After recording and reconstruction of the image datasets the correction is then undertaken, whereby a number of cases are conceivable.

As was also already evident from FIG. 1 for example, all linear operations, especially also the point spread function on the attenuation values, are local so that especially advantageously the correction can be applied locally, especially in regions around artifacts or around structures and risk from artifacts. The regions can be defined automatically and/or manually, whereby the automatic determination is undertaken for example by artifact detection algorithms, but preferably by determination of the position of structures in danger from artifacts, for example larger blood vessels in the case of perfusion measurements, especially on the basis of an anatomical atlas.

Figure 3:
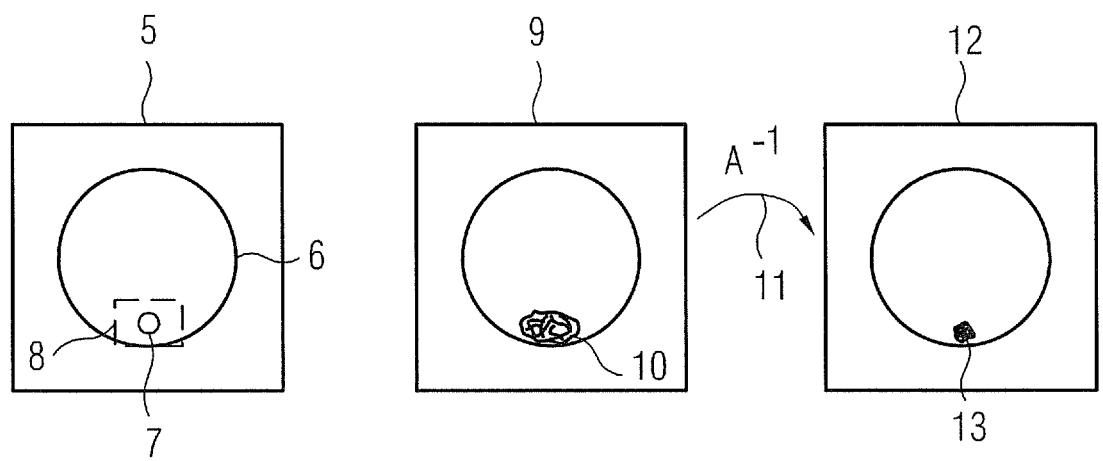

Please refer to FIG. 3 for an example in this context. In this figure the left part of the FIG. 5 shows a section through the head 6, as can occur in an anatomical atlas. An artery 7 is shown by way of example. It can now be assumed that, in a region 8, which can for example be 40 times 40 pixels in size, artifacts can be produced around the artery 7 if a perfusion measurement, for example to determine the blood flow in the brain, is to be carried out.

A reconstructed two-dimensional image dataset 9 in a slice corresponding to the section of the part 5 of the figure which is not yet corrected is shown in the central part of the figure. Evidently the artery 7 cannot be seen since it is surrounded by artifacts 10 as a result of the change in the contrast agent concentration during the recording of the one-dimensional projection images, which can take three seconds for example.

If the matrix A is now determined for the region 8 for example, in which case it can be sufficient in the present instance to only consider the derivations up to the first or the second order, since perfusion time curves can often be approximated sufficiently accurately linearly or quadratically, and if the inverted matrix $A^{-1}$ is now applied to the region 8 in the image dataset 9, arrow 11, the corrected image dataset 12 shown as the right-hand part of the figure is obtained, in which the signals 13 of the artery 7 can be clearly seen since the surrounding artifacts 10 are reduced or even entirely removed.

If the regions in which artifacts are present or can be present is not precisely defined there can be provision as an alternative for the entire image dataset 9 to be divided up into regions which are then each corrected locally per se to facilitate faster computation.

Naturally it is basically also possible to correct the entire image at once.

If the method basically operates with the same imaging parameters and if basically derivations up to the same order are observed or if the applications are able to be subdivided into corresponding groups, the inverted matrix $A^{-1}$ or the number of inverted matrixes $A^{-1}$ are then of course also permanently maintained, for example in a memory unit of the X-ray device in order to then be applied directly.

The invention claimed is:

1. A method for correcting an artifact in an image dataset of a target region, comprising:
   rotationally recording X-ray projection images of the target region at an angular speed;
   reconstructing the image dataset of the target region from the X-ray projection images by filtered back projection;
   determining a linear relationship between attenuation values of the image dataset and real attenuation values from a sum of a point spread function weighted with a temporal derivation evaluated at a reference time and with an inverse of the angular speed;
   inverting the linear relationship; and
   obtaining the real attenuation values by applying the inverted linear relationship to the attenuation values of the image dataset for correcting the artifact in the image dataset.

2. The method as claimed in claim 1, wherein the linear relationship is described by a formula $$a = \left(\sum_i W_i P_i D_i\right) b,$$

wherein a is a vector describing the attenuation values of the image dataset, b is a vector describing the real attenuation values, $W_i$ is a diagonal matrix specifying the weighting factor, $P_i$ is a matrix describing the point spread function and $D_i$ is a matrix describing an ith-order temporal derivation.

3. The method as claimed in claim 1, wherein the inverted linear relationship is determined by a singular value decomposition.

4. The method as claimed in claim 1, wherein the correction is applied locally in a region of the artifact and/or a region of a structure at a risk of the artifact.

5. The method as claimed in claim 4, wherein the region comprises a blood vessel.

6. The method as claimed in claim 4, wherein a position of the structure is determined automatically by an anatomical atlas.

7. The method as claimed in claim 1, wherein the image dataset and/or a selected region of the image dataset is broken down into units to be corrected locally.

8. The method as claimed in claim 1, wherein the image dataset is three-dimensional and the correction is carried out in slices.

9. The method as claimed in claim 1, wherein the rotational recording is carried out within a perfusion imaging.

10. The method as claimed in claim 1, wherein the temporal derivation comprises a first derivation or a second derivation.

11. The method as claimed in claim 1, wherein a real attenuation point described in time by an nth level polynomial is projected forward and the point spread function is determined there from by back projection.

* * * * *